United States Patent
Benting et al.

(10) Patent No.: US 9,445,589 B2
(45) Date of Patent: Sep. 20, 2016

(54) ACTIVE COMPOUNDS COMBINATIONS COMPRISING A LIPO-CHITOOLIGOSACCHARIDE DERIVATIVE AND A NEMATICIDE, INSECTICIDAL OR FUNGICIDAL COMPOUND

(71) Applicant: Bayer CropScience AG, Monheim (DE)

(72) Inventors: Jürgen Benting, Leichlingen (DE); Ruth Meissner, Leverkusen (DE); Jean-Pierre Vors, Sainte-Foy-les-Lyon (FR)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 14/397,752

(22) PCT Filed: May 22, 2013

(86) PCT No.: PCT/EP2013/060452
§ 371 (c)(1),
(2) Date: Oct. 29, 2014

(87) PCT Pub. No.: WO2013/174836
PCT Pub. Date: Nov. 28, 2013

(65) Prior Publication Data
US 2015/0119240 A1 Apr. 30, 2015

Related U.S. Application Data

(60) Provisional application No. 61/669,691, filed on Jul. 10, 2012.

(30) Foreign Application Priority Data

May 22, 2012 (EP) .................................. 12356013

(51) Int. Cl.
| *A01N 43/16* | (2006.01) |
| *A01N 63/02* | (2006.01) |
| *A01N 63/00* | (2006.01) |
| *A01N 51/00* | (2006.01) |
| *A01N 25/00* | (2006.01) |
| *A01N 43/78* | (2006.01) |
| *C07H 5/06* | (2006.01) |

(52) U.S. Cl.
CPC ............... *A01N 43/16* (2013.01); *A01N 25/00* (2013.01); *A01N 43/78* (2013.01); *A01N 51/00* (2013.01); *A01N 63/00* (2013.01); *A01N 63/02* (2013.01); *C07H 5/06* (2013.01); *A01N 2300/00* (2013.01)

(58) Field of Classification Search
CPC ...... A01N 43/16; A01N 63/02; A01N 25/00; A01N 51/00; A01N 63/00; A01N 2300/00; A01N 43/78; C07H 5/06
See application file for complete search history.

(56) References Cited

U.S. PATENT DOCUMENTS

2010/0048404 A1* 2/2010 Hungenberg et al. ........ 504/292

FOREIGN PATENT DOCUMENTS

| WO | WO/2008/071672 A2 | 6/2008 |
| WO | WO/2008/071674 A2 | 6/2008 |
| WO | WO/2009/124707 A2 | 10/2009 |
| WO | WO/2010/125065 A2 | 11/2010 |

OTHER PUBLICATIONS

Jumpstart, Soygreen, and Torque, [online]. Halstead Elevator Company, 2009 [retrieved on Jan. 28, 2016]. Retrieved from the Internet<http://www.halstadelevator.com/images/E0065601/JumpstartSoygreentorque4_9.pdf>, 3 pages.*
International Search Report and Written Opinion of the International Searching Authority, International Patent Application No. PCT/EP2013/060452, Jul. 17, 2013, 11 pages.

* cited by examiner

*Primary Examiner* — John Pak
*Assistant Examiner* — Andriae M Holt
(74) *Attorney, Agent, or Firm* — Adam L. Lunceford; Michelle L. Samonek

(57) ABSTRACT

The present invention relates to active compounds combinations which comprises (A) a lipo-chitooligosaccharide derivative and a further nematicide, insecticidal, acaricide or fungicidal compound (B). The present invention also relates to active compounds combinations which comprises further an additional nematicide, insecticidal, acaricide or fungicidal compound (C). Moreover, the invention relates to a method for curatively or preventively or eradicatively controlling harmful organisms, to a method for increasing yield or stimulating plant growth, to the use of a combination according to the invention for the treatment of seed or plant, to a method for protecting a seed and not at least to the treated seed.

7 Claims, No Drawings

ACTIVE COMPOUNDS COMBINATIONS COMPRISING A LIPO-CHITOOLIGOSACCHARIDE DERIVATIVE AND A NEMATICIDE, INSECTICIDAL OR FUNGICIDAL COMPOUND

CROSS-REFERENCE TO RELATED APPLICATION(S)

The present application is a 35 U.S.C. §371 national phase conversion of PCT/EP2013/060452, filed on May 22, 2013, which claims priority of European Patent Application No. 12356013.8 filed May 22, 2012, and U.S. Patent Application No. 61/669,691, filed on Jul. 10, 2012, each of which is hereby incorporated by reference in its entirety. Applicant claims priority to each of the foregoing patent applications. The PCT International Application was published in the English language.

The present invention relates to active compounds combinations which comprises (A) a lipo-chitooligosaccharide derivative and a further nematicide, insecticidal, acaricide or fungicidal compound (B). The present invention also relates to active compounds combinations which comprises further an additional nematicide, insecticidal, acaricide or fungicidal compound (C).

Moreover, the invention relates to a method for curatively or preventively or eradicatively controlling harmful organisms, to a method for increasing yield or stimulating plant growth, to the use of a combination according to the invention for the treatment of seed or plant, to a method for protecting a seed and not at least to the treated seed.

Lipo-chitooligosaccharide (LCO) derivatives, their preparation and their use in combinations with insecticidal or fungicidal compounds are described in WO 2005/063784, WO2008/071672, WO2008/071674 and WO2010/125065. Nevertheless, the compositions of the present inventions were not disclosed in said patent applications.

Torque™ is a product commercialized by Novozymes which includes a LCO derivative.

Since the environmental and economic requirements imposed on modern-day crop protection compositions are continually increasing, with regard, for example, to the spectrum of action, toxicity, selectivity, application rate, formation of residues, favourable preparation ability, yield increase or plant growth stimulation, and since, furthermore, there may be problems, for example, with resistances, a constant task is to develop new compositions which in some areas at least help to fulfil the abovementioned requirements.

The present invention provides active compounds combinations/compositions which in some aspects at least achieve the stated objective.

It has now been found, surprisingly, that the combinations according to the invention not only bring about the additive enhancement of the spectrum of action that was in principle to be expected but achieves a synergistic effect which extends the range of action of the component (A), of the component (B) and, when applied, of the component (C), in two ways. Firstly, the rates of application of the component (A), of the component (B) and, when applied, of component (C) are lowered whilst the action remains equally good. Secondly, the combination still achieves a high degree of efficiency even where the two or three individual compounds have become ineffective or poorly effective in such a low application rate range. This increases safety in use. The active compounds combinations according to the invention may have further surprising properties which, in a wider sense, may also be called synergistic, such as, for example: broadening of the activity spectrum to other phytopathogens, for example to resistant strains of plant diseases; lower application rates of the active compounds; sufficient control of pests with the aid of the active compounds combinations according to the invention even at application rates where the individual compounds show no or virtually no activity; advantageous behaviour during formulation or during use, for example during grinding, sieving, emulsifying, dissolving or dispensing; improved storage stability and light stability; advantageous residue formation; improved toxicological or ecotoxicological behaviour; improved properties of the plant, for example better growth, increased harvest yields, a better developed root system, a larger leaf area, greener leaves, stronger shoots, less seed required, lower phytotoxicity, mobilization of the defence system of the plant, good compatibility with plants. Thus, the use of the active compounds combinations or compositions according to the invention contributes considerably to keeping young cereal stands healthy, which increases, for example, the winter survival of the cereal seed treated, and also safeguards quality and yield. Moreover, the active compounds combinations according to the invention may contribute to enhanced systemic action. Even if the individual compounds of the combination have no sufficient systemic properties, the active compounds combinations according to the invention may still have this property. In a similar manner, the active compounds combinations according to the invention may result in higher persistency of the action.

Accordingly, the present invention provides a combination comprising:

(A) at least one derivative of formula (I)

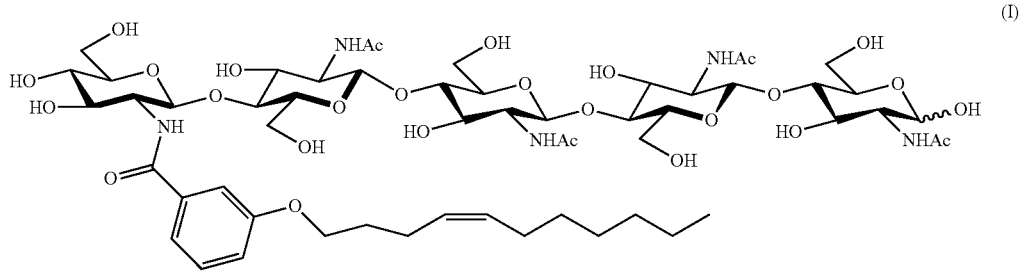

or Torque™;
and (B) at least one compound B selected from the group consisting of products based on *Bacillus firmus* (particularly I-1582 strain) or extract thereof, *Pasteuria* strain or extract thereof, abamectin, fluopyram, thiametoxam, thiodicarb, cyantraniliprole, rynaxypyr, fipronil, ethiprole, 1-(3-chloropyridin-2-yl)-N-[4-cyano-2-methyl-6-(methylcarbamoyl) phenyl]-3-{[5-(trifluoromethyl)-2H-tetrazol-2-yl]methyl}-1H-pyrazole-5-carboxamide, flupyradifurone, mefenoxam, sedaxan, fluoxapyroxad, pyraclostrobin, ipconazol, azoyxystrobin, thiabendazol, methyl-thiophanate.

Torque™ is a product commercialized by Novozymes which includes a LCO (lipo-chitooligosaccharide) derivative.

*Bacillus firmus* I-1582 strain (CNCM I-1582) is a bacteria from soil with nematicide activity, for which Bayer has requested registration (annex I of Directive 91/414/CEE).

SIVANTO™ is an insecticide containing the active ingredient flupyradifurone from the chemical class of butenolides developed by Bayer.

Cyantraniliprole is the active ingredient found in Cyazypyr™.

In a particular embodiment, the product based on *Bacillus firmus* or extract thereof is BioNeem™ or VOTiVO™, particularly VOTiVO™.

BioNeem™ is a biological nematicide commercialized by Agro Green.

VOTiVO™ is a product commercialized by Bayer for offering a nematode protection on the seed. VOTiVO™ is a product based on the naturally soil bacteria, *Bacillus firmus* (strain I-1582) that lives and grows with the plant's root system.

VOTiVO™ is advantageously used in association with Poncho™ or with any other product the active ingredient thereof is clothianidin. Poncho™ refers to a family of compositions (Poncho 1250, Poncho 650, Poncho 500, Poncho 250, ... ) for broad-spectrum insect control commercialized by Bayer. The pesticide clothianidin is the active ingredient of Poncho™. The association Poncho/VOTiVO is particularly used against nematodes.

In a particular embodiment, *Pasteuria* strain is *Pasteuria nishizawae* strain or *Pasteuria reniformis* strain.

In a particular embodiment, the combination according to the invention comprises further a third nematicide, insecticide, acaricide or fungicide compound C which is different from compound B.

In a particular embodiment, compound C is a fungicidal compound selected from:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl) cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy] phenyl}imidoformamide, (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR, 9RS and anti-epimeric racemate 1RS,4SR,9SR) (881685-58-1), (2.12) isopyrazam (anti-epimeric racemate 1RS,4SR, 9SR), (2.13) isopyrazam (anti-epimeric enantiomer 1R,4S, 9S), (2.14) isopyrazam (anti-epimeric enantiomer 1S,4R, 9R), (2.15) isopyrazam (syn epimeric racemate 1RS,4SR, 9RS), (2.16) isopyrazam (syn-epimeric enantiomer 1R,4S, 9R), (2.17) isopyrazam (syn-epimeric enantiomer 1S,4R, 9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazolin-4-amine (1210070-84-0), (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(Difluormethyl)-1-methyl-N-(1,1,3-trimethyl-2,3-dihydro-1H-inden-4-yl)-1H-pyrazol-4-carboxamid, (2.33) 1,3,5-Trimethyl-N-(1,1,3-trimethyl-2,3-dihydro-1H-inden-4-yl)-1H-pyrazol-4-carboxamid, (2.34) 1-Methyl-3-(trifluormethyl)-N-(1,3,3-trimethyl-2,3-dihydro-1H-inden-4-yl)-1H-pyrazol-4-carboxamid, (2.35) 1-Methyl-3-(trifluormethyl)-N-[(1S)-1,3,3-trimethyl-2,3-dihydro-1H-inden-4-yl]-1H-pyrazol-4-carboxamid, (2.36) 1-Methyl-3-(trifluormethyl)-N-[(1R)-1,3,3-trimethyl-2,3-dihydro-1H-inden-4-yl]-1H-pyrazol-4-carboxamid, (2.37) 3-(Difluormethyl)-1-methyl-N-[(3S)-1,1,3-trimethyl-2,3-dihydro-1H-inden-4-yl]-1H-pyrazol-4-carboxamid, (2.38) 3-(Difluormethyl)-1-methyl-N-[(3R)-1,1,3-trimethyl-2,3-dihydro-1H-inden-4-yl]-1H-pyrazol-4-carboxamid, (2.39) 1,3,5-Trimethyl-N-[(3R)-1,1,3-trimethyl-2,3-dihydro-1H-inden-4-yl]-1H-pyrazol-4-carboxamid, (2.40) 1,3,5-Trimethyl-N-[(3S)-1,1,3-trimethyl-2,3-dihydro-1H-inden-4-yl]-1H-pyrazol-4-carboxamid.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2), (3.9) famoxadone (131807-57-3), (3.10) fenamidone (161326-34-7), (3.11) fenoxystrobin (918162-02-4), (3.12) fluoxastrobin (361377-29-9), (3.13) kresoxim-methyl (143390-89-0), (3.14) metominostrobin (133408-50-1), (3.15) orysastrobin (189892-69-1), (3.16) picoxystrobin (117428-22-5), (3.17) pyraclostrobin (175013-18-0), (3.18) pyrametostrobin (915410-70-7), (3.19) pyraoxystrobin (862588-11-2), (3.20) pyribencarb (799247-52-2), (3.21) triclopyricarb (902760-40-1), (3.22) trifloxystrobin (141517-21-7), (3.23) (2E)-2-(2-{[6-(3-chloro-2-methylphenoxy)-5-fluoropyrimidin-4-yl]oxy}phenyl)-2-(methoxyimino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenyl)ethanamide, (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl(2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0), (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3), (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7), (5.34) ziram (137-30-4).

(6) Compounds capable to induce a host defence, like for example (6.1) acibenzolar-S-methyl (135158-54-2), (6.2) isotianil (224049-04-1), (6.3) probenazole (27605-76-1), (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0), (7.8) 3-(5-fluoro-3,3,4,4-tetramethyl-3,4-dihydroisoquinolin-1-yl)quinoline (861647-32-7).

(8) Inhibitors of the ATP production, for example (8.1) fentin acetate (900-95-8), (8.2) fentin chloride (639-58-7), (8.3) fentin hydroxide (76-87-9), (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8), (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0), (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2), (11.7) 2,2,2-trifluoroethyl {3-methyl-1-[(4-methylbenzoyl)amino]butan-2-yl}carbamate (851524-22-6).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3), (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7), (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6), (14.5) meptyldinocap (131-72-6).

(15) Further compounds, like for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2), (15.54) 1-(4-{4-[(5R)-5-(2,6-difluorophenyl)-4,5-dihydro-1,2-oxazol-3-1,3-thiazol-2-yl}piperidin-1-yl)-2-[5-methyl-3-(trifluoromethyl)-1H-pyrazol-1-yl]ethanone (1003319-79-6), (15.55) 1-(4-{4(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4), (15.75) 5-fluoro-2-[(4-methylbenzyl)oxy]pyrimidin-4-amine (1174376-25-0), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N—{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]1,3-thiazole-4-carboxamide (922514-48-5), (15.90) pentyl {6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6), (15.94) tert-butyl {6-[({[(1-methyl-1H-tetrazol-5-yl)(phenyl)methylene]amino}oxy)methyl]pyridin-2-yl}carbamate;

(16) Further compounds, like for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl)biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide, (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl)biphenyl-2-yl]-1,3-dimethyl-1H-pyrazole-4-carboxamide, (16.17) 2-chloro-N-[4'-(3-hydroxy-3-methylbut-1-yn-1-yl)biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl)biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid, (16.24) but-3-yn-1-yl {6-[({[(Z)-(1-methyl-1H-tetrazol-5-yl)(phenyl)methylene]amino}oxy)methyl]pyridin-2-yl}carbamate, (16.25) 4-Amino-5-fluorpyrimidin-2-ol (mesomere Form: 6-Amino-5-fluorpyrimidin-2(1H)-on), (16.26) propyl 3,4,5-trihydroxybenzoate.

All named mixing partners of the classes (1) to (16) can, if their functional groups enable this, optionally form salts with suitable bases or acids.

In an other particular embodiment, compound C is a insecticidal, nematicide or acaricide compound selected from:

(1) Acetylcholinesterase (AChE) inhibitors, for example
carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or
organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, and Vamidothion.

(2) GABA-gated chloride channel antagonists, for example
cyclodiene organochlorines, e.g. Chlordane and Endosulfan; or
phenylpyrazoles (fiproles), e.g. Ethiprole and Fipronil.

(3) Sodium channel modulators/voltage-dependent sodium channel blockers, for example pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, and Transfluthrin; or
DDT; or Methoxychlor.

(4) Nicotinic acetylcholine receptor (nAChR) agonists, for example
neonicotinoids, e.g. Acetamiprid, Clothianidin, Dinotefuran, Imidacloprid, Nitenpyram, Thiacloprid, and Thiamethoxam; or
Nicotine; or
Sulfoxaflor.

(5) Nicotinic acetylcholine receptor (nAChR) allosteric activators, for example
spinosyns, e.g. Spinetoram and Spinosad.

(6) Chloride channel activators, for example
avermectins/milbemycins, e.g. Abamectin, Emamectin benzoate, Lepimectin, and Milbemectin.

(7) Juvenile hormone mimics, for example
juvenile hormon analogues, e.g. Hydroprene, Kinoprene, and Methoprene; or
Fenoxycarb; or Pyriproxyfen.

(8) Miscellaneous non-specific (multi-site) inhibitors, for example
alkyl halides, e.g. Methyl bromide and other alkyl halides; or
Chloropicrin; or Sulfuryl fluoride; or Borax; or Tartar emetic.

(9) Selective homopteran feeding blockers, e.g. Pymetrozine; or Flonicamid.

(10) Mite growth inhibitors, e.g. Clofentezine, Hexythiazox, and Diflovidazin; or
Etoxazole.

(11) Microbial disruptors of insect midgut membranes, e.g. *Bacillus thuringiensis* subspecies *israelensis*, *Bacillus thuringiensis* subspecies *aizawai*, *Bacillus thuringiensis* subspecies *kurstaki*, *Bacillus thuringiensis* subspecies *tenebrionis*, and B.t. crop proteins: Cry1Ab, Cry1Ac, Cry1Fa, Cry1A.105, Cry2Ab, Vip3A, mCry3A, Cry3Ab, Cry3Bb, Cry34 Ab1/35Ab1; or
*Bacillus sphaericus*.

(12) Inhibitors of mitochondrial ATP synthase, for example Diafenthiuron; or
organotin miticides, e.g. Azocyclotin, Cyhexatin, and Fenbutatin oxide; or Propargite; or Tetradifon.

(13) Uncouplers of oxidative phoshorylation via disruption of the proton gradient, for example Chlorfenapyr, DNOC, and Sulfluramid.

(14) Nicotinic acetylcholine receptor (nAChR) channel blockers, for example Bensultap, Cartap hydrochloride, Thiocyclam, and Thiosultap-sodium.

(15) Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron, and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide, and Tebufenozide.

(19) Octopamine receptor agonists, for example Amitraz.

(20) Mitochondrial complex III electron transport inhibitors, for example Hydramethylnon; or Acequinocyl; or Fluacrypyrim.

(21) Mitochondrial complex I electron transport inhibitors, for example
METI acaricides, e.g. Fenazaquin, Fenpyroximate, Pyrimidifen, Pyridaben, Tebufenpyrad, and Tolfenpyrad; or
Rotenone (Derris).

(22) Voltage-dependent sodium channel blockers, e.g. Indoxacarb; or Metaflumizone.

(23) Inhibitors of acetyl CoA carboxylase, for example
tetronic and tetramic acid derivatives, e.g. Spirodiclofen, Spiromesifen, and Spirotetramat.

(24) Mitochondrial complex IV electron transport inhibitors, for example
phosphines, e.g. Aluminium phosphide, Calcium phosphide, Phosphine, and Zinc phosphide; or
Cyanide.

(25) Mitochondrial complex II electron transport inhibitors, for example beta-ketonitrile derivatives, e.g. Cyenopyrafen and Cyflumetofen.

(28) Ryanodine receptor modulators, for example
diamides, e.g. Chlorantraniliprole, Cyantraniliprole, and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, and iodomethane; furthermore products based on *Bacillus firmus* (including but not limited to strain CNCM I-1582 or extract thereof, such as, for example, VOTiVO™, BioNem) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl](cyclopropyl)amino}furan-2(5H)-one (known from WO2007/115643), 4-{[(6-chloropyridin-3-yl)methyl](cyclopropyl)amino}furan-2(5H)-one (known from EP-A-0 539 588), 4-{[(6-chlorpyridin-3-yl)methyl](methyl) amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and its diastereomers {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (also known from WO2007/149134) as well as diastereomers [(R)-methyl(oxido){(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-$\lambda^4$-sulfanylidene]cyanamide (A2), referred to as group of diastereomers A (known from WO2010/074747, WO2010/074751), [(R)-methyl(oxido) (1S)-1-[6-(trifluoromethyl)pyridin-3-yl]ethyl-$\lambda^4$-sulfanylidene]cyanamide (B1) and [(S)-methyl (oxido){(1R)-1-[6-(trifluoromethyl)pyridin-3-yl]ethyl}-$\lambda^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluorethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethyl-benzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl) malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2- trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl(methyl)amino}-1,3-oxazol-2(5H)-one (all known from WO2010/005692), N-[4-(1,1,1,3,3,3-hexafluoro-2-methoxypropan-2-yl)-3-isobutylphenyl]-N-isobutyryl-1,3,5-trimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl) ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

In a particular embodiment, said further nematicide, insecticide, acaricide or fungicide compound C is selected from the group consisting of products based on *Bacillus firmus* or extract thereof (particularly I-1582 strain or extract thereof, BioNeem or VOTiVO™), *Pasteuria* strain (particularly *Pasteuria nishizawae* strain or *Pasteuria reniformis* strain) or extract thereof, abamectin, fluopyram, clothianidin, imidacloprid, thiametoxam, thiodicarb, cyantraniliprole, rynaxypyr, fipronil, ethiprole, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, flupyradifurone, metalaxyl, mefenoxam, metalaxyl M, penflufen, sedaxan, fluoxapyroxad, prothioconazole, tebuconazole, fludioxinil, trifloxystrobin, pyraclostrobin, ipconazol, azoyxystrobin, thiabendazol, methyl-thiophanate.

In a particular embodiment, the combination of the invention consists of a compound A of formula (I) as herein described or Torque™ and an active compound B selected from the group consisting of products based on *Bacillus firmus* or extract thereof (particularly I-1582 strain or extract thereof, BioNeem or VOTiVO™), *Pasteuria* strain (particularly *Pasteuria nishizawae* strain or *Pasteuria reniformis* strain) or extract thereof, abamectin, fluopyram, thiametoxam, thiodicarb, cyantraniliprole, rynaxypyr, fipronil, ethiprole, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, flupyradifurone, mefenoxam, sedaxan, fluoxapyroxad, pyraclostrobin, ipconazol, azoyxystrobin, thiabendazol, methyl-thiophanate.

In a particular embodiment, the combination of the invention consists of a compound A of formula (I) as herein described or Torque™, an active compound B selected from the group consisting of products based on *Bacillus firmus* or extract thereof (particularly I-1582 strain or extract thereof, BioNeem or VOTiVO™), *Pasteuria* strain (particularly *Pasteuria nishizawae* strain or *Pasteuria reniformis* strain) or extract thereof, abamectin, fluopyram, thiametoxam, thiodicarb, cyantraniliprole, rynaxypyr, fipronil, ethiprole, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, flupyradifurone, mefenoxam, sedaxan, fluoxapyroxad, pyraclostrobin, ipconazol, azoyxystrobin, thiabendazol, methyl-thiophanate and a nematicide, insecticide, acaricide or fungicide compound C different from compound B.

In a particular embodiment, the combination of the invention consists of a compound A of formula (I) as herein described or Torque™, an active compound B selected from the group consisting of products based on *Bacillus firmus* or extract thereof (particularly I-1582 strain or extract thereof, BioNeem or VOTiVO™), abamectin, *Pasteuria* strain (particularly *Pasteuria nishizawae* strain or *Pasteuria reniformis* strain) or extract thereof, fluopyram, thiametoxam, thiodicarb, cyantraniliprole, rynaxypyr, fipronil, ethiprole, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, flupyradifurone, mefenoxam, sedaxan, fluoxapyroxad, pyraclostrobin, ipconazol, azoyxystrobin, thiabendazol, methyl-thiophanate and an active compound C different from compound B, wherein compound C is selected from the group consisting of products based on *Bacillus firmus* or extract thereof (particulalrly I-1582 strain or extract thereof, BioNeem or VOTiVO™), abamectin, *Pasteuria* strain (particularly *Pasteuria nishizawae* strain or *Pasteuria reniformis* strain) or extract thereof, fluopyram, clothianidin, imidacloprid, thiametoxam, thiodicarb, cyantraniliprole, rynaxypyr, fipronil, ethiprole, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, flupyradifurone, metalaxyl, mefenoxam, metalaxyl M, penflufen, sedaxan, fluoxapyroxad, prothioconazole, tebuconazole, fludioxinil, trifloxystrobin, pyraclostrobin, ipconazol, azoxystrobin, thiabendazol, methyl-thiophanate.

In a particular embodiment, the combination of the invention comprises a) the compound A of formula (I) as herein described or Torque™ and b) a product based on *Bacillus firmus* or extract thereof.

In a particular embodiment, the combination of the invention comprises a) the compound A of formula (I) as herein described or Torque™, b) a product based on *Bacillus firmus* or extract thereof, and c) clothianidin.

In a particular embodiment, the combination of the invention comprises a) the compound A of formula (I) as herein described and b) a product based on *Bacillus firmus* or extract thereof.

In a particular embodiment, the combination of the invention comprises a) the compound A of formula (I) as herein described, b) a product based on *Bacillus firmus* or extract thereof and c) clothianidin.

In a particular embodiment, the combination of the invention comprises a) the compound A of formula (I) as herein described or Torque™ and b) VOTiVO™.

In a particular embodiment, the combination of the invention comprises a) the compound A of formula (I) as herein described or Torque™, b) VOTiVO™, and c) clothianidin.

In a particular embodiment, the combination of the invention comprises a) the compound A of formula (I) as herein described and b) VOTiVO™.

In a particular embodiment, the combination of the invention comprises a) the compound A of formula (I) as herein described, b) VOTiVO™, and c) clothianidin.

In the context of the invention, clothianidin is advantageously provided by the use of Poncho™, a pesticide product commercialized by Bayer. Clothianidin is the active ingredient of Poncho™.

If the active compounds in the active compounds combinations according to the invention are present in certain weight ratios, the synergistic effect is particularly pronounced. However, the weight ratios of the active compounds in the active compounds combinations can be varied within a relatively wide range.

In the combinations according to the invention the compounds (A) and (B) are preferably present in a synergistically effective weight ratio of AB in a range from 1/1 to $1/10^{10}$, from 1/1 to $1/10^9$, from 1/10 to $1/10^8$, from $1/10^2$ to $1/10^7$, from $1/10^3$ to $1/10^6$.

In the combinations according to the invention the compounds (A), (B) and (C) are preferably present in a synergistically effective weight ratio of A/B/C in a range from 1/1/1 to $1/10^{10}/10^{11}$, from 1/1/10 to $1/10^9/10^{10}$, from $1/10/10^2$ to $1/10^8/10^9$, from $1/10^2/10^3$ to $1/10^7/10^8$, from $1/10^3/10^4$ to $1/10^6/10^7$.

When the combinations according to the invention are used for seed treatment, compound (A) may preferably be applied in a synergistically effective concentration of $10^{-4}$ to $10^4$ mg/100 kg of seed, of $10^{-3}$ to $10^3$ mg/100 kg of seed, of $10^{-2}$ to $10^2$ mg/100 kg of seed; compound (B) may preferably be applied in a synergistically effective concentration of $10^{-2}$ to $10^5$ g/100 kg of seed, of $10^{-1}$ to $10^4$ g/100 kg of seed, of 1 to $10^3$ g/100 kg of seed; compound (C), when present, may preferably be applied in a synergistically effective concentration of $10^{-1}$ to $10^6$ g/100 kg of seed, of 1 to $10^5$ g/100 kg of seed, of 10 to $10^4$ g/100 kg of seed.

Where a compound (A) or a compound (B) can be present in tautomeric form, such a compound is understood hereinabove and hereinbelow also to include, where applicable, corresponding tautomeric forms, even when these are not specifically mentioned in each case.

Compounds (A) or compounds (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$-alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$-alkane- or arylsulfonic acids, e.g. methane- or p-toluene-sulfonic acid. Compounds (A) or compounds (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propyl-amine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compounds (A) or the compounds (B) in free form and in the form of their salts, hereinabove and herein below any reference to the free compounds (A) or free compounds (B) or to their salts should be understood as including also the corresponding salts or the free compounds (A) or free compounds (B), respectively, where appropriate and expedient. The equivalent also applies to tautomers of compounds (A) or compounds (B) and to their salts.

According to the invention the expression "combination" stands for the various combinations of compounds (A) and (B), or (A), (B) and (C), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (A), (B), and eventually (C) is not essential for working the present invention.

The present invention furthermore relates to compositions for combating/controlling undesirable microorganisms comprising the active compounds combinations according to the invention. Preferably, the compositions are fungicidal, insecticidal, acaricide or nematicide compositions comprising agriculturally suitable auxiliaries, solvents, carriers, surfactants or extenders.

Furthermore the invention relates to a method of combating undesirable microorganisms, characterized in that the active compounds combinations according to the invention are applied to the phytopathogenic fungi, insects or nematodes and/or their habitat.

The present invention furthermore relates to compositions for increasing the yield or for stimulating the plant growth comprising the active compounds combinations according to the invention.

Furthermore the invention relates to a method for increasing the yield or for stimulating the plant growth, characterized in that the active compounds combinations according to the invention are applied to the plant.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulfoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty esters of polyols, and derivatives of the compounds containing sulfates, sulfonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight, 0.01 and 98 percent by weight, preferable between 0.1 and 95 percent by weight, particularly preferred between 0.5 and 90 percent by weight of the active compounds combination according to the invention, very particularly preferable between 10 and 70 percent by weight.

The active compounds combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compounds combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The compositions according to the invention do not only comprise ready-to-use compositions which can be applied with suitable apparatus to the plant or the seed, but also commercial concentrates which have to be diluted with water prior to use.

The active compounds combinations according to the invention can be present in (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and Semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

The invention furthermore comprises a method for treating seed. The invention furthermore relates to seed treated according to one of the methods described in the preceding paragraph.

The active compounds or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions. There is also a great interest in having active compounds, as for example compounds capable of stimulating the yield or plant growth, in contact with the seed.

The control of harmful organisms by treating the seed of plants has been known for a long time and is the subject of continuous improvements. However, the treatment of seed entails a series of problems which cannot always be solved in a satisfactory manner Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by harmful organisms, but without damaging the plant itself by the active compound employed. In particular, methods for the treatment of seed should also take into consideration the intrinsic properties of transgenic plants in order to achieve optimum protection of the seed and the germinating plant with a minimum of crop protection agents being employed.

Accordingly, the present invention also relates in particular to a method for protecting seed and germinating plants against attack by harmful organisms by treating the seed with a composition according to the invention. The invention also relates to the use of the compositions according to the invention for treating seed for protecting the seed and the germinating plant against harmful organisms. Furthermore, the invention relates to seed treated with a composition according to the invention for protection against harmful organisms.

The present invention also relates in particular to a method for increasing the plant yield or stimulating the plant growth by treating the seed with a composition according to the invention. The invention also relates to the use of the compositions according to the invention for treating seed for increasing the plant yield or stimulating the plant growth. Furthermore, the invention relates to seed treated with a composition according to the invention.

The control of harmful organisms which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from harmful organisms. In this manner, the immediate treatment of the crop at the time of sowing or shortly thereafter can be dispensed with.

It is also considered to be advantageous that the mixtures according to the invention can be used in particular also for transgenic seed where the plant growing from this seed is capable of expressing a protein which acts against pests. By treating such seed with the active compounds combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture or viticulture. In particular, this takes the form of seed of cereals (such as wheat, barley, rye, triticale, millet, oats), maize (corn), cotton, soya bean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants (also see below). The treatment of seeds of cereals (such as wheat, barley, rye, triticale, and oats), maize (corn) and rice is of particular importance.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica carinata*, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak choi, kohlrabi, radish, horseradish, cress, Chinese cabbage), Leguminosae sp. (for instance peanuts, peas and beans beans—such as climbing beans and broad beans), Chenopodiaceae sp. (for instance marigold, spinach beet, spinach, beetroots), Malvaceae (for instance okra), Asparagaceae (for instance asparagus); horticultural and forest crops; ornamental plants; as well as genetically modified homologues of these crops.

In a particular embodiment, combination according to the invention is used to treat corn, soybean or cotton plant, or seed thereof.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference-RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compounds combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the above-mentioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. No. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. No. 11/517,991, 10/739,610, 12/139,408, 12/352,532, 11/312, 866, 11/315,678, 12/421,292, 11/400,598, 11/651,752, 11/681,285, 11/605,824, 12/468,205, 11/760,570, 11/762, 526, 11/769,327, 11/769,255, 11/943801 or 12/362,774. Plants comprising other genes that confer glyphosate tolerance, such as decarboxylase genes, are described in e.g. U.S. patent application Ser. No. 11/588,811, 11/185,342, 12/364, 724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646, 024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at:

http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at:

http://www.lifesci.sussex.ac.uldhome/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549 b) Plants, such as cotton plants, containing an altered form of rsw2 or rsw3 homologous nucleic acids as described in WO 2004/053219 c) Plants, such as cotton plants, with increased expression of sucrose phosphate synthase as described in WO 01/17333 d) Plants, such as cotton plants, with increased expression of sucrose synthase as described in WO 02/45485 e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938 f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947 b) Plants such as oilseed rape plants, producing oil having a low linolenic acid content as described in U.S. Pat. No. 6,270,828, U.S. Pat. No. 6,169,190, or U.S. Pat. No. 5,965,755 c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 WO09/068313 and WO10/006732.

Particularly useful transgenic plants which may be treated according to the invention are plants containing transformation events, or combination of transformation events, that are the subject of petitions for nonregulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 2006/128569); Event 1143-51B (cotton, insect control, not deposited, described in WO 2006/128570); Event 1445 (cotton, herbicide tolerance, not deposited, described in US-A 2002-120964 or WO 02/034946); Event 17053 (rice, herbicide tolerance, deposited as PTA-9843, described in WO 2010/117737); Event 17314 (rice, herbicide tolerance, deposited as PTA-9844, described in WO 2010/117735); Event 281-24-236 (cotton, insect control-herbicide tolerance, deposited as PTA-6233, described in WO 2005/103266 or US-A 2005-216969); Event 3006-210-23 (cotton, insect control-herbicide tolerance, deposited as PTA-6233, described in US-A 2007-143876 or WO 2005/103266); Event 3272 (corn, quality trait, deposited as PTA-9972, described in WO 2006/098952 or US-A 2006-230473); Event 40416 (corn, insect control-herbicide tolerance, deposited as ATCC PTA-11508, described in WO 2011/075593); Event 43A47 (corn, insect control-herbicide tolerance, deposited as ATCC PTA-11509, described in WO 2011/075595); Event 5307 (corn, insect control, deposited as ATCC PTA-9561, described in WO 2010/077816); Event ASR-368 (bent grass, herbicide tolerance, deposited as ATCC PTA-4816, described in US-A 2006-162007 or WO 2004/053062); Event B16 (corn, herbicide tolerance, not deposited, described in US-A 2003-126634); Event BPS-CV127-9 (soybean, herbicide tolerance, deposited as NCIMB No. 41603, described in WO 2010/080829); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO 2006/128571); Event CE46-02A (cotton, insect control, not deposited, described in WO 2006/128572); Event COT102 (cotton, insect control, not deposited, described in US-A 2006-130175 or WO 2004/039986); Event COT202 (cotton, insect control, not deposited, described in US-A 2007-067868 or WO 2005/054479); Event COT203 (cotton, insect control, not deposited, described in WO 2005/054480); Event DAS40278 (corn, herbicide tolerance, deposited as ATCC PTA-10244, described in WO 2011/022469); Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO 2009/100188); Event DAS68416 (soybean, herbicide tolerance, deposited as ATCC PTA-10442, described in WO 2011/066384 or WO 2011/066360); Event DP-098140-6 (corn, herbicide tolerance, deposited as ATCC PTA-8296, described in US-A 2009-137395 or WO 2008/112019); Event DP-305423-1 (soybean, quality trait, not deposited, described in US-A 2008-312082 or WO 2008/054747); Event DP-32138-1 (corn, hybridization system, deposited as ATCC PTA-9158, described in US-A 2009-0210970 or WO 2009/103049); Event DP-356043-5 (soybean, herbicide tolerance, deposited as ATCC PTA-8287, described in US-A 2010-0184079 or WO 2008/002872); Event EE-1 (brinjal, insect control, not deposited, described in WO 2007/091277); Event FI117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control-herbicide tolerance, deposited as ATCC PTA-8398, described in WO 2008/151780); Event GHB614 (cotton, herbicide tolerance, deposited as ATCC PTA-6878, described in US-A 2010-050282 or WO 2007/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO 2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC- 23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 2005/061720); Event MIR162 (corn, insect control, deposited as PTA-8166, described in US-A 2009-300784 or WO 2007/142840); Event MIR604 (corn, insect control, not deposited, described in US-A 2008-167456 or WO 2005/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 2004/011601 or US-A 2006-095986); Event MON87427 (corn, pollination control, deposited as ATCC PTA-7899, described in WO 2011/062904); Event MON87460 (corn, stress tolerance, deposited as ATCC PTA-8910, described in WO 2009/111263 or US-A 2011-0138504); Event MON87701 (soybean, insect control, deposited as ATCC PTA-8194, described in US-A 2009-130071 or WO 2009/064652); Event MON87705 (soybean, quality trait-herbicide tolerance, deposited as ATCC PTA-9241, described in US-A 2010-0080887 or WO 2010/037016); Event MON87708 (soybean, herbicide tolerance, deposited as ATCC PTA9670, described in WO 2011/034704); Event MON87754 (soybean, quality trait, deposited as ATCC PTA-9385, described in WO 2010/024976); Event MON87769 (soybean, quality trait, deposited as ATCC PTA-8911, described in US-A 2011-0067141 or WO 2009/102873); Event MON88017 (corn, insect control-herbicide tolerance, deposited as ATCC PTA-5582, described in US-A 2008-028482 or WO 2005/059103); Event MON88913 (cotton, herbicide tolerance, deposited as ATCC PTA-4854, described in WO 2004/072235 or US-A 2006-059590); Event MON89034 (corn, insect control, deposited as ATCC PTA-7455, described in WO 2007/140256 or US-A 2008-260932); Event MON89788 (soybean, herbicide tolerance, deposited as ATCC PTA-6708, described in US-A 2006-282915 or WO 2006/130436); Event MS11 (oilseed rape, pollination control-herbicide tolerance, deposited as ATCC PTA-850 or PTA-2485, described in WO 01/031042); Event MS8 (oilseed rape, pollination control-herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 2008/114282); Event RF3 (oilseed rape, pollination control-herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control-herbicide tolerance, deposited as ATCC PTA-8171, described in US-A 2010-077501 or WO 2008/122406); Event T342-142 (cotton, insect control, not deposited, described in WO 2006/128568); Event TC1507 (corn, insect control-herbicide tolerance, not deposited, described in US-A 2005-039226 or WO 2004/099447); Event VIP1034 (corn, insect control-herbicide tolerance, deposited as ATCC PTA-3925, described in WO 03/052073), Event 32316 (corn, insect control-herbicide tolerance, deposited as PTA-11507, described in WO 2011/084632), Event 4114 (corn, insect control-herbicide tolerance, deposited as PTA-11506, described in WO 2011/084621).

In the context of the present invention, the active compounds combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds combinations which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compounds combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1. Suitable wetting agents that may be present in the seed dressing formulations which can be used according to the invention include all substances which promote wetting and are customary in the formulation of active agrochemical substances. With preference it is possible to use alkylnaphthalene-sulfonates, such as diisopropyl- or diisobutylnaphthalene-sulfonates.

Suitable dispersants and/or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulfated derivatives. Particularly suitable anionic dispersants are lignosulfonates, polyacrylic salts, and arylsulfonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The active compounds or compositions according to the invention have strong microbicidal activity and can be used for controlling unwanted microorganisms, such as fungi and bacteria, in crop protection and material protection.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

The compositions according to the invention can be used for the curative or protective control of harmful organisms. Accordingly, the invention also relates to curative and protective methods for controlling harmful organisms using the active compounds combinations or compositions according to the invention, which are applied to the seed, the plant or plant parts, the fruit or the soil in which the plants grow. Preference is given to application onto the plant or the plant parts, the fruits or the soil in which the plants grow.

The compositions according to the invention for combating harmful organisms in crop protection comprise an active, but non-phytotoxic amount of the compounds according to the invention. "Active, but non-phytotoxic amount" shall mean an amount of the composition according to the invention which is sufficient to control or to completely kill the plant disease, which amount at the same time does not exhibit noteworthy symptoms of phytotoxicity. These application rates generally may be varied in a broader range, which rate depends on several factors, e.g. the harmful organism, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and seed, and of the soil.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant variety protection rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds. Preference is given to the treatment of the plants and the above-ground and below-ground parts and organs of the plants, such as shoot, leaf, flower and root, examples which may be mentioned being leaves, needles, stems, trunks, flowers, and fruits.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material. They may be preferably employed as crop protection agents. They are active against normally sensitive and resistant species and against all or some stages of development.

The following plants may be mentioned as plants which can be treated according to the invention: cotton, flax, grapevines, fruit, vegetable, such as Rosaceae sp. (for example pomaceous fruit, such as apples and pears, but also stone fruit, such as apricots, cherries, almonds and peaches and soft fruit such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit), Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumbers), Alliaceae sp. (for example leek, onions), Papilionaceae sp. (for example peas); major crop plants, such Gramineae sp. (for example maize, lawn, cereals such as wheat, rye, rice, barley, oats, millet and triticale), Asteraceae sp. (for example sunflowers), Brassicaceae sp. (for example white cabbage, red cabbage, broccoli, cauliflowers, Brussels sprouts, pak choi, kohlrabi, garden radish, and also oilseed rape, mustard, horseradish and cress), Fabacae sp. (for example beans, peas, peanuts), Papilionaceae sp. (for example soya beans), Solanaceae sp. (for example potatoes), Chenopodiaceae sp. (for example sugar beet, fodder beet, Swiss chard, beetroot); crop plants and ornamental plants in garden and forest; and also in each case genetically modified varieties of these plants.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

In material protection the substances of the invention may be used for the protection of technical materials against infestation and destruction by harmful organisms.

Technical materials are understood to be in the present context non-living materials that have been prepared for use in engineering. For example, technical materials that are to be protected against micro-biological change or destruction by the active materials of the invention can be adhesives, glues, paper and cardboard, textiles, carpets, leather, wood, paint and plastic articles, cooling lubricants and other materials that can be infested or destroyed by micro-organisms. Within the context of materials to be protected are also parts of production plants and buildings, for example cooling circuits, cooling and heating systems, air conditioning and ventilation systems, which can be adversely affected by the propagation of harmful organisms, particularly fungi and/or microorganisms. Within the context of the present invention, preferably mentioned as technical materials are adhesives, glues, paper and cardboard, leather, wood, paints, cooling lubricants and heat exchanger liquids, particularly preferred is wood. The combinations according to the invention can prevent disadvantageous effects like decaying, dis- and decoloring, or molding. The active compounds combinations and compositions according to the invention can likewise be employed for protecting against colonization of objects, in particular ship hulls, sieves, nets, buildings, quays and signalling installations, which are in contact with sea water or brackish water.

The method of treatment according to the invention can also be used in the field of protecting storage goods against attack of harmful organisms, particularly fungi and microorganisms. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata; Guignardia* species, such as, for example, *Guignardia bidwelli; Leptosphaeria* species, such as, for example, *Leptosphaeria maculans; Magnaporthe* species, such as, for example, *Magnaporthe grisea; Microdochium* species, such as, for example, *Microdochium nivale; Mycosphaerella* species, such as, for example, *Mycosphaerella graminicola* and *M. fijiensis; Phaeosphaeria* species, such as, for example, *Phaeosphaeria nodorum; Pyrenophora* species, such as, for example, *Pyrenophora teres; Ramularia* species, such as, for example, *Ramularia collo-cygni; Rhynchosporium* species, such as, for example, *Rhynchosporium secalis; Septoria* species, such as, for example, *Septoria apii; Typhula* species, such as, for example, *Typhula incarnata; Venturia* species, such as, for example, *Venturia inaequalis;*

Root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Tapesia* species, such as, for example, *Tapesia acuformis; Thielaviopsis* species, such as, for example, *Thielaviopsis basicola;*

Ear and panicle diseases (including maize cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as for example, *Septoria nodorum;*

Diseases caused by smut fungi, such as, for example, *Sphacelotheca* species, such as, for example, *Sphacelotheca reiliana; Tilletia* species, such as, for example, *Tilletia caries; T. controversa; Urocystis* species, such as, for example, *Urocystis occulta; Ustilago* species, such as, for example, *Ustilago nuda; U. nuda tritici;*

Fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *P. purpurogenum; Sclerotinia* species, such as, for example, *Sclerotinia sclerotiorum; Verticilium* species, such as, for example, *Verticilium alboatrum;*

Seed- and soil-borne rot and wilt diseases, and also diseases of seedlings, caused, for example, by *Fusarium* species, such as, for example, *Fusarium culmorum; Phytophthora* species, such as, for example, *Phytophthora cactorum; Pythium* species, such as, for example, *Pythium ultimum; Rhizoctonia* species, such as, for example, *Rhizoctonia solani; Sclerotium* species, such as, for example, *Sclerotium rolfsii;*

Cancerous diseases, galls and witches' broom caused, for example, by *Nectria* species, such as, for example, *Nectria galligena;*

Wilt diseases caused, for example, by *Monilinia* species, such as, for example, *Monilinia laxa;*

Deformations of leaves, flowers and fruits caused, for example, by *Taphrina* species, such as, for example, *Taphrina deformans;*

Degenerative diseases of woody plants caused, for example, by *Esca* species, such as, for example, *Phaemoniella clamydospora* and *Phaeoacremonium aleophilum* and *Fomitiporia mediterranea;*

Diseases of flowers and seeds caused, for example, by *Botrytis* species, such as, for example, *Botrytis cinerea;*

Diseases of plant tubers caused, for example, by *Rhizoctonia* species, such as, for example, *Rhizoctonia solani; Helminthosporium* species, such as, for example, *Helminthosporium solani;*

Diseases caused by bacteriopathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora.*

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae. Microorganisms of the following genera may be mentioned as examples: *Alternaria*, such as *Alternaria tenuis, Aspergillus*, such as *Aspergillus niger, Chaetomium*, such as *Chaetomium globosum, Coniophora*, such as *Coniophora puetana, Lentinus*, such as *Lentinus tigrinus, Penicillium*, such as *Penicillium glaucum, Polyporus*, such as *Polyporus versicolor, Aureobasidium*, such as *Aureobasidium pullulans, Sclerophoma*, such as *Sclerophoma pityophila, Trichoderma*, such as *Trichoderma*

*viride, Escherichia*, such as *Escherichia coli, Pseudomonas*, such as *Pseudomonas aeruginosa*, and *Staphylococcus*, such as *Staphylococcus aureus*.

In addition, the compounds of the formula (I) or Torque™ according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi by no means limits the mycotic spectrum which can be covered, but is only for illustration.

When applying the compounds according to the invention the application rates can be varied within a broad range. The dose of active compound/application rate usually applied in the method of treatment according to the invention is generally and advantageously for treatment of part of plants, e.g. leafs (foliar treatment): from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against harmful organisms and/or pests and/or phytopathogenic fungi and/or microorganisms. The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxins, Patuline, Ergotalkaloides und Aflatoxines, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudo graminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The present invention further relates to a composition as herein-defined comprising at least one further active ingredient selected from the group of the insecticides, attractants, sterilants, bactericides, acaricides, nematicides, fungicides, growth regulators, herbicides, fertilizers, safeners and semiochemicals.

In particular, said further active ingredient can be chosen in the lists of insecticides, attractants, sterilants, bactericides, acaricides, nematicides, fungicides, growth regulators, herbicides, fertilizers, safeners and semiochemicals disclosed herein.

The present invention further relates to a method for controlling harmful organisms and/or increasing the yield and/or stimulating the growth, characterized in that an active compounds combination as herein-defined is applied to the harmful organisms and/or their habitat.

The present invention further relates to a process for producing compositions for controlling harmful organisms and/or increasing the yield and/or stimulating the growth, characterized in that an active compounds combination as herein-defined is mixed with extenders and/or surfactants.

The present invention further relates to the use of an active compounds combination as herein-defined for controlling harmful organisms and/or increasing the yield and/or stimulating the growth.

The present invention further relates to the use of an active compounds combination as herein-defined for the treatment of transgenic plants.

The present invention further relates to the use of an active compounds combination as herein-defined for the treatment of seed and of seed of transgenic plants.

The present invention further relates to the use of an active compounds combination as herein-defined for the foliar treatment of plants or transgenic plants.

The advanced activity of the active compounds combinations according to the invention is evident from the example below.

A synergistic effect is always present when the activity of the active compounds combinations exceeds the total of the activities of the active compounds when applied individually. The expected activity for a given combination of two active compounds can be calculated as follows (cf. Colby, S. R., "Calculating Synergistic and Antagonistic Responses of Herbicide Combinations", *Weeds* 1967, 15, 20-22):

If

X is the efficacy when active compound A is applied at an application rate of x ppm (or g/ha), Y is the efficacy when active compound B is applied at an application rate of y ppm (or g/ha), E is the efficacy when the active compounds A and B are applied at application rates of x and y ppm (or g/ha), respectively, and then $$E = X + Y - \frac{X * Y}{100}$$

If the actual activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.*, 1964, 70, 73-80).

The invention is illustrated by the following example. However the invention is not limited to the example.

EXAMPLE 1

Maize Seedlings Shoot Weight

Maize seeds are grown in loamy sand in the greenhouse at 20 C and 70% humidity for 11 days. After 11 days seedlings were cut off above the soil and fresh weight was determined. Compounds are applied at the following concentration:

Poncho™ (pesticidal product comprising clothianidin as active ingredient): 250 µg of clothianidin/kernel;
VOTiVO™ (product based on the natural soil bacteria *Bacillus firmus* (strain I-1582): 50 µg/kernel;
Compound A of formula (I): 0.01 µg/kernel.

The test is evaluated 11 days after the application. 100% means shoot weight which corresponds to that of the untreated control. Efficacy means in this case the additional % of shoot weight in comparison to that of the untreated control.

|  | Seedling shoot weight (g) (Average on 3 replicates) | Found % | Efficacy % | Calculated % |
|---|---|---|---|---|
| Untreated control | 14.3 | 100 | | |
| Poncho ™ (clothianidin) | 13.7 | 96 | | |
| VOTiVO ™ | 13.6 | 95.3 | | |
| Compound A of formula (I) | 15.3 | 107 | 7 | |
| Poncho ™ + VOTiVO ™ | 15.0 | 107 | 7 | |
| Compound A of formula (I) + Poncho ™ + VOTiVO ™ | 16.8 | 118 | 18 | 13 |

The invention claimed is:

1. An active compounds composition comprising
(A) one derivative compound of formula (I)

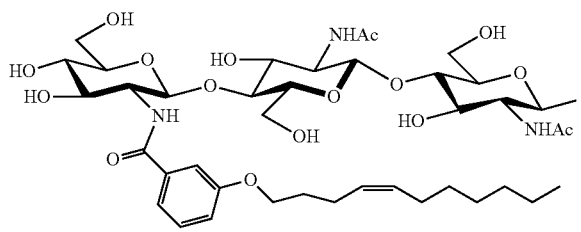

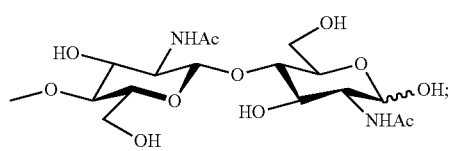

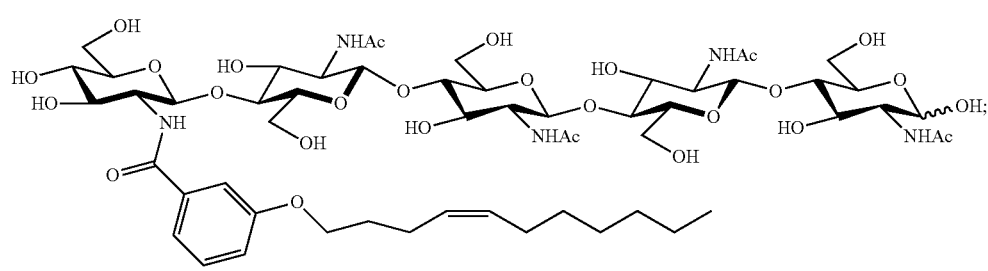

(B) *Bacillus firmus* strain I-1582; and
(C) clothianidin
in a synergistically effective weight ratio of A/B/C in a range from $1/10^3/10^4$ to $1/10^6/10^7$.

2. The composition according to claim 1 further comprising extenders and/or surfactants.

3. The composition according to claim 2 comprising at least one further active ingredient selected from the group consisting of insecticides, attractants, sterilants, bactericides, acaricides, nematicides, fungicides, growth regulators, herbicides, fertilizers, safeners and semiochemicals.

4. A seed treated with an active compounds composition according to claim 1.

5. A method for controlling harmful organisms, characterized in that an active compounds composition according to claim 1 is applied to the harmful organisms and/or their habitat.

6. A method for increasing yield or stimulating plant growth, characterized in that an active compounds composition according to claim 1 is applied to the plant.

7. A process for producing compositions characterized in that an active compounds composition according to claim 1 is mixed with extenders and/or surfactants.

* * * * *